United States Patent
Mao et al.

(10) Patent No.: US 6,708,052 B1
(45) Date of Patent: Mar. 16, 2004

(54) METHOD AND APPARATUS FOR CARDIAC IMAGING WITH MINIMIZED CARDIAC MOTION ARTIFACT

(75) Inventors: Songshou Mao, Torrance, CA (US); Matthew J. Budoff, Redondo Beach, CA (US)

(73) Assignee: Harbor UCLA Research and Education Institute, Torrance, CA (US)

( * ) Notice: Subject to any disclaimer, the term of this patent is extended or adjusted under 35 U.S.C. 154(b) by 167 days.

(21) Appl. No.: 09/833,461

(22) Filed: Apr. 11, 2001

(51) Int. Cl.⁷ .............................. A61B 6/00; A61B 6/03; G01N 23/00
(52) U.S. Cl. .............................. 600/407; 378/8; 378/95
(58) Field of Search ................................ 600/407, 409, 600/411, 415, 425, 427; 378/4, 8, 12, 15, 21, 23, 95, 98.5, 901

(56) References Cited

U.S. PATENT DOCUMENTS

| | | | |
|---|---|---|---|
| 4,547,892 A | * | 10/1985 | Richey et al. ............. 378/8 |
| 4,868,747 A | * | 9/1989 | Mori et al. ............. 378/901 |
| 5,751,782 A | * | 5/1998 | Yoshitome ............. 378/98.5 |
| 6,154,516 A | * | 11/2000 | Heuscher et al. ............. 378/15 |
| 6,252,924 B1 | * | 6/2001 | Davantes et al. ............. 378/8 |
| 6,256,368 B1 | * | 7/2001 | Hsieh et al. ............. 378/8 |
| 6,393,091 B1 | * | 5/2002 | Slack et al. ............. 378/8 |

FOREIGN PATENT DOCUMENTS

EP  1090586 A2 * 4/2001

* cited by examiner

*Primary Examiner*—Willis R. Wolfe
(74) *Attorney, Agent, or Firm*—Orrick, Herrington & Sutcliffe LLP

(57) ABSTRACT

The present invention provides for a method and apparatus for acquiring cardiac images having minimized motion artifact by triggering an image-acquisition scan at a point during the quiescent segment of each cardiac cycle. The method of the present invention comprises: measuring the length of the R-R interval of a cardiac cycle; calculating the R-T segment length based on gender and R-R interval length; identifying an optimal scan starting point of the cardiac cycle based on R-R interval length, R-T segment length and scan speed; and triggering the image-acquisition scan at this starting segment. The method is implemented by an apparatus, namely a cardiac imaging device that has image-acquisition speeds of about 15–300 ms. The apparatus comprises a transmitter that generates the image-acquisition signal, an input console, and an ECG gating device that synchronizes the trigger of image-acquisition scans with the starting points determined by the above method.

24 Claims, 2 Drawing Sheets

METHOD AND APPARATUS FOR CARDIAC IMAGING WITH MINIMIZED CARDIAC MOTION ARTIFACT

FIELD OF THE INVENTION

The present invention relates generally to cardiac imaging and, in particular, acquiring cardiac images having minimized motion artifact with high-speed imaging devices. The invention relates to a method and apparatus for acquiring these cardiac images by prospective gating based in part on the length of a cardiac cycle, gender of the subject being imaged and the imaging speed.

BACKGROUND OF THE INVENTION

Acquiring clear images of the heart is typically impeded by cardiac motion and coronary artery motion caused by the rhythmic beating of the heart. The resulting loss of resolution causes blurring or streaking, called motion artifact, which diminishes the diagnostic value of these images.

Efforts have been made to minimize cardiac motion artifact. Scanning protocols may be adapted to attempt to limit the motion reflected in the cardiac image. Alternatively, patients may simply be instructed to lie still and hold their breath during the scan to reduce respiratory motion, or patient restraints and supports may be used to limit general body motion. In addition, some attempts have been made to shorten image acquisition time by actively increasing the subject's heart rate and/or increasing the speed of the image-acquisition scan generated by the cardiac imaging device. As an alternative, ECG gating techniques have developed which involve equipping the cardiac imaging apparatus with an ECG gating device that synchronizes the image-acquisition scans with specific phases of the cardiac cycle.

ECG gating relies on the electrocardiographic signals that represent the rhythmic contraction of the heart's atria and ventricles. These signals originate from electrical pulses of the sinoatrial (SA) node, which spread over the atria and ventricles and cause them to contract, resulting in a complete cycle of the heart's contractions. Thus, a recorded ECG waveform represents the cardiac cycle, and is comprised of a set of discrete electrocardiographic signals corresponding to the muscular contraction and relaxation of the atria and ventricles. Specifically, the R-R interval measures the period of the heart beat, the P-R segment corresponds to the time from the onset of atrial contraction to the onset of ventricular contraction; the R-T segment approximately measures ventricular contraction or systole; and the T-R interval measures ventricular relaxation, or diastole.

Many known ECG gating techniques involve "retrospective triggers" that coordinate the scanning of images with different electrocardiographic signals of the cardiac cycle to obtain a full set of scans over a number of cardiac cycles. Then, the scans are "sorted" by computerized means according to the phase of the cycle during which they were taken to construct separate images of each phase of the cardiac cycle. Thereafter, the technician or physician selects the clearest image from this series with the least motion artifact for diagnostic purposes.

ECG gating techniques also involve efforts to "prospectively trigger" an image-acquisition scan starting with a specific phase of the cardiac cycle, typically at 40–50% of the R-R interval and at 70–80% of the R-R interval. These percentages allegedly correspond to quiescent points of the cardiac cycle where cardiac motion is at a minimum.

There are several problems associated with known ECG gating techniques. First, the traditional techniques generate scan triggers at pre-determined, fixed percentages of the cardiac cycle regardless of the heart rate of the subject being imaged during the scanning procedure. Quiescent points, however, vary with heart rate, so that using a fixed percentage for all subjects regardless of heart rate is ineffective.

Moreover, with many known techniques, the clarity of the resulting images depends on the type of imaging device being used and the speed of the image-acquisition scan it generates. For instance, one ECG gating technique involves using 40–50% of the R-R interval to trigger image-acquisition scan for coronary artery screening or coronary angiography with electron beam tomography (EBT), which has an ultrashort image acquisition time (50–100 ms). This technique may not be as effective with scanning devices having longer acquisition times, such as MRI and spiral CT scanners (100–500 ms).

Finally, because the traditional techniques generate triggers at pre-determined percentages of the R-R interval, the length of each cardiac cycle must be the same during the scanning procedure so that the image-acquisition scan is triggered at precisely the right time for each heart beat. Thus, these techniques produce images with minimized motion artifact only when the heart being imaged has a consistent heart rate, usually measured in beats per minute. ECG gating is not effective for those subjects that have irregular heart rates, or whose heart rates increase or decrease during the imaging procedure, either because of a physical condition or disease or because of stress resulting from the imaging procedure.

Thus, it is an object of the present invention to provide a method and apparatus for acquiring diagnostically valuable cardiac images of the heart having minimized motion artifact via prospective gating by triggering an image-acquisition scan starting at a point of a cardiac cycle, where this point is calculated, in part, by the length of the cardiac cycle. It is yet another object of the present invention to acquire cardiac images having minimized motion artifact with imaging devices having a wide range of scan speeds. Finally, it is an object of this invention to acquire these diagnostically valuable cardiac images in a manner wherein the quality of the resulting images is not dependent on consistent heart rate and, in fact, may dynamically vary as necessary with each heart beat.

SUMMARY OF THE INVENTION

The present invention relates to a method and apparatus for acquiring an image of the heart by triggering an image-acquisition scan starting at a point of the cardiac cycle having minimized motion. The optimal point for triggering an image-acquisition scan is determined by measuring the lengths of the cardiac cycles of the subject being imaged. The optimal trigger point of each cardiac cycle depends on the length of that cycle; thus, this point varies as the length of the cardiac cycle changes. Thus, preferably, the present method and apparatus measures each cardiac cycle during the scanning procedure and dynamically determines and adjusts the optimal trigger point from one heart beat to the next as necessary. Thus, in the preferred embodiment, the diagnostic value of the images obtained pursuant to this invention does not rely on the subject having a constant heart rate throughout the duration of the scanning procedure.

The method disclosed by the present invention acquires a cardiac image with minimized motion artifact by measuring the length of the R-R interval of a particular heart beat, calculating the length of the R-T segment to determine the quiescent segment of the cardiac cycle, identifying an optimal scan starting point of the cardiac cycle, and triggering an image-acquisition scan at this point.

The calculation of the R-T segment length is based in part on the gender of the subject and the length of the R-R interval. For men, the R-T length is calculated by the algorithm 0.143×RR+224.2; for women, the R-T length is calculated by the algorithm 0.157×RR+221.2. In both cases, the R-R interval=1000 ms×60/heart rate (ms). The quiescent segment, which corresponds to the period of minimized cardiac motion velocity, is late systole to early diastole, and approximates the end of the R-T segment.

The optimal scan starting point, which is within the quiescent segment, is based on the image-acquisition scan speed and the subject's heart rate. The present method contemplates the use of scan speeds that fall within the range of about 25 ms to about 250 ms. As an example, the optimal scan starting point is at 25–50 ms before the end of the R-T interval where the speed of the scan protocol is 25–100 ms for any heart rate. However, this scan starting point is suboptimal where the scan protocol speed is over 150 ms and the subject's heart rate is less than 61 beats per minute. In this case, mid-diastole provides for better scan points because the longer quiescent segment is at 60–80% of the R-R interval. Thus, the optimal scan starting point will vary with each subject's heart rate and the imaging device used. The optimal scan starting point in the R-R interval is identified by the algorithm RS=RT±X, where RS refers to the length of time from the peak of the R wave to the scan starting point, the length of the RT segment is determined by the formulas set forth above, and the "X" value depends on the scan speed, as listed in table 1 herein.

The present method is implemented by a cardiac imaging apparatus that is capable of generating image-acquisition scans within the range of about 15 ms to about 300 ms, namely MRI devices, spiral CT scanners and EBT scanners. The apparatus comprises a transmitter that generates the image-acquisition scan, an input console that receives parameters used in implementing the above method, and an ECG gating device that is connected to and adapted to communicate with the transmitter and the input console. This gating device synchronizes the triggering of image-acquisition scans with specific points of the cardiac cycle. The ECG gating device includes hardware that receives electrical signals representing the cardiac cycle and triggers image-acquisition scans. The ECG gating device also preferably includes software that operates the gating hardware and is adapted to implement many of the steps described above, i.e., to measure the length of the R-R interval, calculate the length of the R-T segment and to identify the optimal scan starting point. Alternatively, these steps towards identification of the optimal scan starting point may be implemented manually by the physician or technician overseeing the scanning procedure who can relay the calculated optimal scan starting point to the ECG gating device via the input console. Regardless of how this optimal scan starting point is relayed to the gating hardware, it electronically triggers the transmitter to release an image-acquisition scan at that point.

This and further objects and advantages of will be apparent to those skilled in the art in connection with the drawings and the detailed description set forth below.

DETAILED DESCRIPTION OF THE PREFERRED EMBODIMENTS

Figure 1:
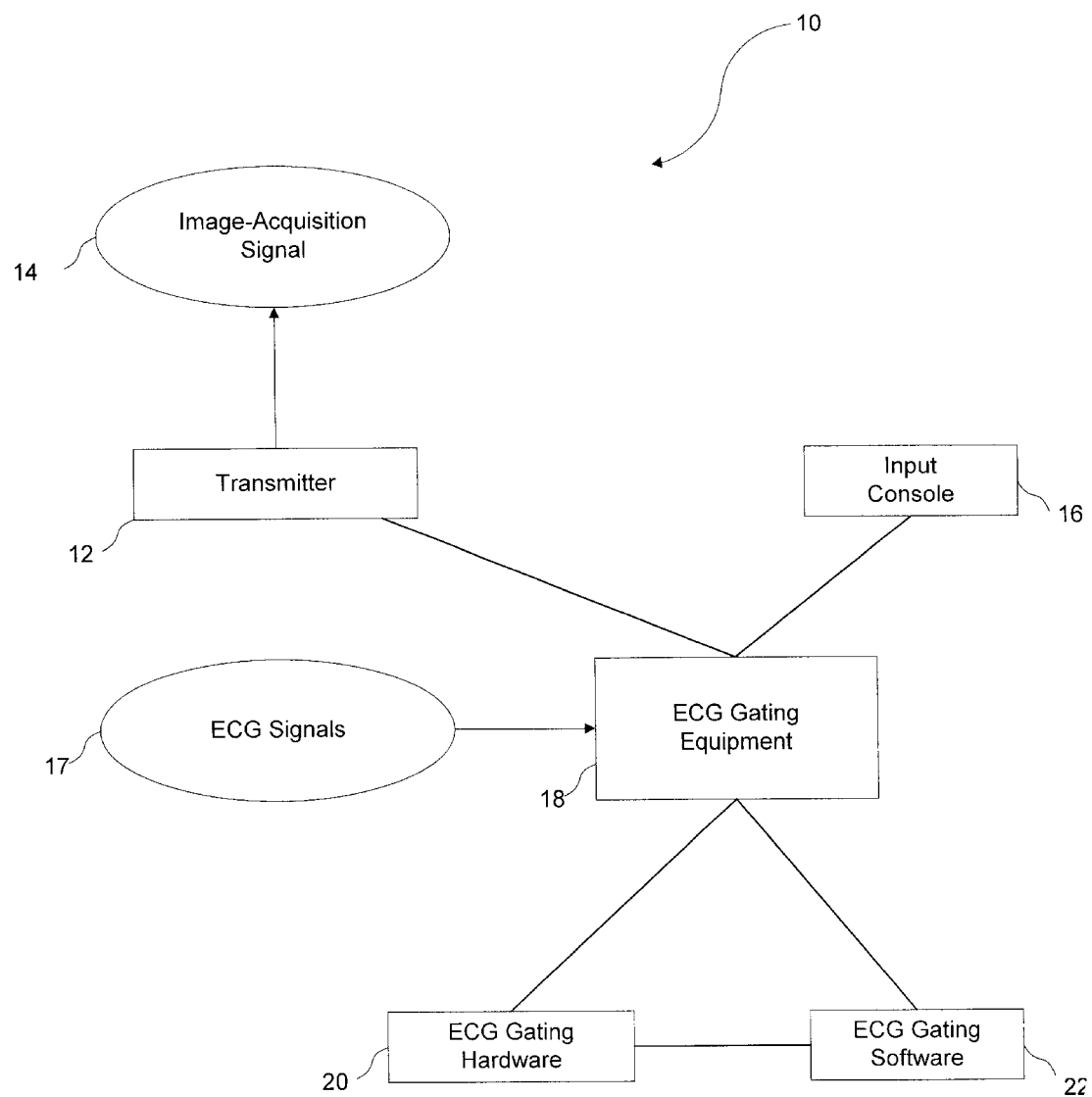
FIG. 1 is a flowchart of the method of the present invention.

The present invention discloses a method for acquiring an image of the heart by triggering an image-acquisition scan at a point in the cardiac cycle having minimized motion artifact, whereby the trigger point is based on the length of the cardiac cycle. As seen in FIG. 1, the method is implemented by a cardiac imaging apparatus 10 that receives the subject's electrocardiographic signals, receives the optimal scan starting point of each heartbeat, and triggers the image-acquisition scan at that point.

This invention contemplates the use of a cardiac imaging apparatus capable of generating high-speed image-acquisition scans, i.e., magnetic resonance imaging devices (MRI's) provided by companies such as GE and Siemens, electron beam tomography (EBT) scanners provided by companies such as Imatron, and spiral computer tomography (spiral CT) scanners provided by GE, Siemens, Toshiba, Picker, Phillips, Marconi and other manufacturers. These devices vary in the components involved in acquiring images.

These devices also share several general features in common. Cardiac imaging apparatus 10 contemplated by the present invention, whether it comprises a MRI device, a spiral CT scanner or EBT scanner, includes a transmitter 12 that generates an image-acquisition electrical scan 14. In an MRI, transmitter 12 comprises an RF pulse transmitter; in spiral CT and EBT scanners, transmitter 12 comprises a x-ray tube and x-ray gun, respectively. Also included in apparatus 10 is input console 16 that allows the technician or physician to enter parameters used in practicing the invention and to receive data from the apparatus. Finally, imaging apparatus 10 also contains ECG gating equipment 18 that is connected to and adapted to communicate with other components of apparatus 10, including transmitter 12 and input console 16, to synchronize image acquisition with the cardiac cycle. This ECG gating equipment includes electrode leads attached to the subject and an ECG telemetric system that acquire the electrocardiogram signals 17. Received signals 17 are then routed to ECG gating hardware 20 that contains digital and analog connectors and related circuitry to trigger image-acquisition scan 14.

EGG gating equipment 18 also preferably includes a software program 22 that operates hardware 20, and that receives and processes parameters used in practicing the invention, as described in more detail below. Program 22 applies these parameters according to the steps set forth below to calculate the point of each heart beat at which to trigger image-acquisition scan 14, and instructs gating hardware 20 of this trigger point. In this way, the invention may achieve one of the preferred objectives, i.e., to determine the length of each cardiac cycle during the scanning procedure and to dynamically vary the optimal scan starting point as necessary with each heart beat.

While the description set forth herein refers to this preferred embodiment, wherein steps 26, 28 and 30 of the claimed method are implemented automatically for each heart beat by program 22, this invention also contemplates implementing steps 26, 28 and 30 manually, by the physician or technician overseeing the scanning procedure. The term "manually" includes, by way of example and not limitation, via manual calculation, calculator or computer-assisted means. That is, the physician/technician may take the heart rate of the subject being imaged immediately prior to the scanning procedure and, from this, calculate the average R-R length using, for example, the R-R=100 ms×60/heart rate (ms) formula described above. The physician/technician may then calculate the R-T segment length and the R-S segment length by the steps described in more detail below.

Figure 2:
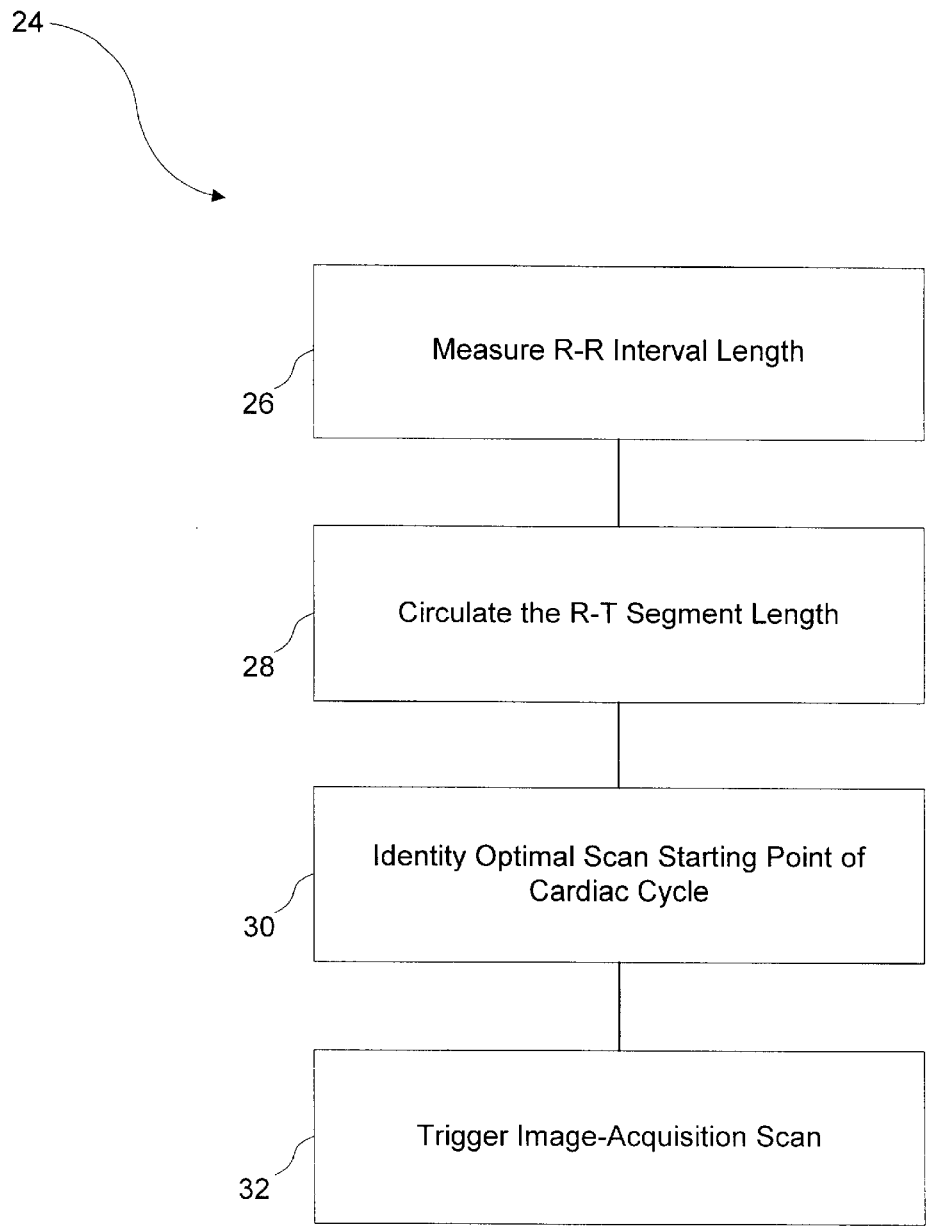
FIG. 2 is a block diagram of the apparatus of the present invention.

Referring to FIG. 2, the method 24 of the present invention begins with preparing the subject for ECG measurements of the heart by attaching standard electrode leads to the subject's chest and electrically connecting them to ECG gating equipment 18. The first step, step 26, is to measure the length of the R-R interval of a particular heart beat of the subject. This step is preferably implemented by software 22 that is programmed to automatically measure the time period in ms between two R electrocardiogram waveforms. A normal heart beats 60–80 times/minute, which translates into about 1000 ms/beat to about 750 ms/beat. However, there is wide variation in possible R-R waveform lengths. Subjects with bradycardyia can have heart rates as slow as 40 (or under) beats/minute, or about 1500 ms/beat, while subjects with tachycardia can have heart rates as fast as 110 beats/minute, or 545 ms/beat. The R-R waveform length is stored by ECG gating equipment 18.

Next, in step 28, the length of the R-T segment of the heart beat is calculated. The length of this segment is important because, as described above, it reflects the period of systole or ventricular contraction. More importantly, the R-T segment reflects late systole, and the end of the T wave corresponds to the quiescent segment of the cardiac cycle. Typically, the value of R-T length ranges from 24% to 54% of the cardiac cycles in subjects with heart rates from 35–115 beats per minute.

In calculating the R-T segment, gender is relevant, i.e., women have been found to have longer R-T intervals than men. In addition, significant correlation was found between heart rate and the length of the R-T segment. As heart rate increased from about 40 beats/min to about 110 beats/min and the R-R interval length decreased, the R-T segment—i.e., the period of systole—also became shorter. Thus, based on these findings, the R-T segment of the cardiac cycle of a subject is the function of the subject's gender and R-R interval length. For a male subject, the R-T length may be calculated by: RT=0.143×RR+224.2. For a female subject, the R-T length calculation is: RT=0.157×RR+221.2. The RT values fall typically between 350–365 ms for subjects with normal heart rate (60–80 beats per minutes).

Calculation of the length of the R-T segment may be implemented by input console 16 and software program 22 where a technician or physician enters the subject's gender into console 16. Then, program 22 selects the appropriate algorithm based on the subject's gender and inputs the R-R value measured in step 26. The R-T segment length is stored by ECG gating equipment 18.

Next, in step 30, the optimal scan starting point of the cardiac cycle is identified. From this point, an image may be acquired with minimized motion artifact. While the end of the R-T segment has been found to correspond to low cardiac motion, as described above, step 30 is also based on cardiac cycle length and, thereby, may factor in potential variation in the length of each heart beat. Thus, the optimal scan starting point at which to trigger the image-acquisition scan may preferably change from one beat to the next. Step 30 also factors in the speed of image-acquisition scan 14, which depends on the imaging device being used, and recognizes that this scan speed may effect the optimal scan starting point for image acquisition. In particular, step 30 effectively determines this optimal scan starting point where the length of the image-acquisition scan is between about 15 ms and about 300 ms, including MRI devices provided by companies such as GE and Siemens, EBT scanners, such as the Imatron EBT machine, and spiral CT scanners provided by companies such as such as GE and Siemens. While the fastest scan speeds generated by these devices to date approximate 50 ms, some have shown the potential of reaching even faster speeds, such as 25 ms.

Thus, step 30 calculates the time period from the R wave to the optimal scan starting point at which to begin the image-acquisition (referred herein as the R-S interval) by the algorithm R-S=RT±X. The optimal scan starting point typically falls before the end of the T wave for most scan protocols. Where the subject being imaged has an extremely slow heart rate and the imaging device being used has a very slow scan speed, the optimal scan starting point has been found to fall beyond the end of the T wave, as exemplified by Table 1. The value of X is a function of the length of the particular heart beat and the speed of the scan being used, and can be determined from the following distribution:

TABLE 1

| HR beats/minute | RR Interval ms | Scan Time 50 ms (15–75 ms) RS = RT ± X | Scan Time 100 ms (76–150 ms) RS = RT ± X | Scan Time 200 ms (151–225 ms) RS = RT ± X | Scan Time 250 ms (226–300 ms) RS = RT ± X |
|---|---|---|---|---|---|
| <40 (Mean 35) | 1714 | RT-25 | RT-50 | RT + 654 | RT + 620 |
| 41–50 (Mean 45) | 1333 | RT-25 | RT-50 | RT + 458 | RT + 432 |
| 51–60 (Mean 55) | 1090 | RT-25 | RT-50 | RT + 300 | RT + 267 |
| 61–70 (Mean 65) | 923 | RT-25 | RT-50 | RT-113 | RT-122 |
| 71–80 (Mean 75) | 800 | RT-25 | RT-50 | RT-102 | RT-126 |
| 81–90 (Mean 85) | 706 | RT-25 | RT-50 | RT-88 | RT-116 |
| 91–100 (Mean 95) | 632 | RT-25 | RT-50 | RT-80 | RT-106 |
| 101–110 (Mean 105) | 571 | RT-25 | RT-50 | RT-68 | RT-91 |
| >110 (Mean 115) | 522 | RT-25 | RT-50 | RT-68 | RT-89 |

Step 30 would also preferably be implemented by input console 16 and software program 22. That is, program 22 would be adapted to read the speed of the imaging scan or, alternatively, the technician or physician would input the speed of the image-acquisition scan into console 16, and program 22 would apply this scan speed and the value of the R-R interval measured in step 26 to determine the value of X. Then, program 22 would plug in the length of the R-T segment calculated in step 28 into algorithm R-S=RT±X to identify the optimal scan starting point.

The next step, step 32, comprises triggering the image-acquisition scan at the optimal scan starting point identified in the above step. As previously described, the triggering of this scan depends on cardiac cycle length and, preferably, may vary dynamically from one heart beat to the next. Step 32 is implemented by ECG gating hardware 20. As soon as program 22 completes steps 26, 28 and 30, thereby identifying the optimal scan starting point, it instructs hardware 20 to electronically trigger transmitter 12 to generate image-acquisition scan 14 at that point. Alternatively, where steps 26, 28 and 30 are implemented without program 22, the physician or technician may relay the optimal scan starting point to hardware 20 via input console 16, which then triggers image-acquisition scan 14.

While preferred method and apparatus embodiments have been shown and described, it will be apparent to one of ordinary skill in the art that numerous alterations may be made without departing from the spirit or scope of the invention. The invention is not to be limited except in accordance with the following claims and their legal equivalents.

We claim:

1. A method for acquiring an image of the heart of a patient by prospectively triggering an image-acquisition scan at a point of a cardiac cycle having minimized motion, comprising:

measuring the length of the R-R interval of said cardiac cycle;

calculating the length of the R-T segment of said cardiac cycle to determine the quiescent segment of said cardiac cycle;

identifying an optimal scan starting point of said cardiac cycle; and prospectively triggering said image-acquisition scan at said optimal scan starting point.

2. The method of claim 1 wherein the speed of said image-acquisition scan is within the range of about 15 ms to about 75 ms.

3. The method of claim 1 wherein the speed of said image-acquisition scan is within the range of about 76 ms to about 150 ms.

4. The method of claim 1 wherein the speed of said image-acquisition scan is within the range of about 151 ms to about 225 ms.

5. The method of claim 1 wherein the speed of said image-acquisition scan is within the range of about 226 ms to about 300 ms.

6. The method of claim 1 wherein said optimal scan starting point is identified in party by said R-R interval length, said R-T segment length, and the speed of said image-acquisition scan.

7. The method of claim 6 wherein the step of identifying said optimal scan starting point comprises applying the algorithm RT±X, where said X value depends on said R-R interval length and the speed of said image-acquisition scan.

8. The method of claim 1 whereby said optimal scan starting point may dynamically vary with each cardiac cycle.

9. The method of claim 8 wherein acquiring said image of the heart is independent of the consistent heart rate of said patient.

10. The method of claim 1 wherein the step of calculating said R-T segment length includes determining the gender of said patient and said R-R interval length.

11. The method of claim 10 wherein the step of calculating said R-T segment length comprises applying the algorithm $0.143 \times RR + 224.2$, where the gender of said patient is male.

12. The method of claim 10 wherein the step of calculating said R-T segment length comprises applying the algorithm $0.157 \times RR + 221.2$, where the gender of said patient is female.

13. A cardiac imaging apparatus that acquires an image of the heart of a patient by prospectively triggering an image-acquisition scan at a point of the cardiac cycle having minimized motion comprising:

a transmitter that generates said image-acquisition scan;

an input console, whereby said input console is adapted to receive information regarding an optimal scan starting point of said cardiac cycle, and said optimal scan starting point is based in part on the length of the R-R interval of said cardiac cycle, the length of the R-T segment of said cardiac cycle, and the speed of said image-acquisition scan;

an ECG gating device that is connected to and adapted to communicate with said transmitter and said input console, whereby said gating device prospectively triggers said image-acquisition scan at said optimal scan starting point.

14. The apparatus of claim 13 comprising a magnetic resonance imaging device.

15. The apparatus of claim 13 comprising a spiral computer tomography scanner.

16. The apparatus of claim 13 comprising an electron beam tomography scanner.

17. The apparatus of claim 13 wherein said ECG gating devices receives and stores the gender of said patient.

18. The apparatus of claim 13 wherein said ECG gating devices receives and stores the speed of said image-acquisition scan.

19. The apparatus of claim 13 wherein said optimal scan starting point is identified by the algorithm RT±X, where said X value depends on said R-R interval length and said image-acquisition scan speed.

20. The apparatus of claim 13 wherein said ECG gating device includes software adapted to measure said R-R interval length, calculate said R-T segment length, and identify said optimal scan starting point.

21. The apparatus of claim 20 wherein said optimal scan starting point may dramatically vary with each cardiac cycle.

22. The apparatus of claim 13 wherein said R-T segment length is based on said R-R interval length and the gender of said patient.

23. The apparatus of claim 22 wherein said R-T segment length is calculated by the algorithm $0.143 \times RR + 224.2$ where the patient is male.

24. The apparatus of claim 22 wherein said R-T segment length is calculated by the algorithm $0.157 \times RR + 221.2$ where the patient is female.

\* \* \* \* \*